United States Patent [19]

Brandt

[11] Patent Number: 5,211,154
[45] Date of Patent: May 18, 1993

[54] METHOD AND APPARATUS FOR MAINTAINING STOICHIOMETRIC AIR-TO-FUEL RATIO IN AN INTERNAL COMBUSTION ENGINE

[75] Inventor: Arnold W. Brandt, Livonia, Mich.

[73] Assignee: Ford Motor Company, Dearborn, Mich.

[21] Appl. No.: 968,133

[22] Filed: Oct. 29, 1992

[51] Int. Cl.[5] .............................................. F02M 7/00
[52] U.S. Cl. .................................... 123/693; 123/406
[58] Field of Search ............... 123/693, 434, 672, 676, 123/694, 695; 204/406, 427, 153.18, 14, 425, 410, 412; 73/23

[56] References Cited

U.S. PATENT DOCUMENTS

| | | | |
|---|---|---|---|
| 4,153,023 | 5/1979 | Asano et al. | 123/693 |
| 4,214,563 | 7/1980 | Hosaka | 123/693 |
| 4,344,317 | 8/1982 | Hattori et al. | 73/23 |
| 4,355,615 | 10/1982 | Asano et al. | 123/693 |
| 4,658,790 | 4/1987 | Kitahara | 123/693 |
| 4,698,209 | 10/1987 | Hashimoto et al. | 204/412 |
| 4,707,241 | 11/1987 | Nakagawa et al. | 204/406 |
| 4,721,084 | 1/1988 | Kawanabe et al. | 123/693 |
| 4,841,934 | 6/1989 | Logothetis et al. | 204/14 |
| 4,891,121 | 1/1990 | Hirako et al. | 204/406 |
| 4,891,122 | 1/1990 | Danno et al. | 204/406 |
| 4,897,174 | 1/1990 | Wang et al. | 204/425 |
| 4,915,813 | 4/1990 | Nakajima et al. | 204/406 |
| 4,915,814 | 4/1990 | Harada et al. | 204/425 |
| 4,981,125 | 1/1991 | Kato et al. | 123/693 |
| 4,990,235 | 2/1991 | Chujo | 204/424 |
| 5,031,445 | 7/1991 | Kato et al. | 73/23.31 |
| 5,037,526 | 8/1991 | Kato et al. | 204/428 |
| 5,039,972 | 8/1991 | Kato et al. | 338/34 |

*Primary Examiner*—Raymond A. Nelli
*Attorney, Agent, or Firm*—Roger L. May; Allan J. Lippa

[57] ABSTRACT

This invention provides an self-calibrating buffer amplifier for a Universal Exhaust Gas Oxygen sensor interface circuit which couples and processes a voltage signal proportional to pumping cell current to a level and reference voltage suitable for input to an A-to-D convertor. The goal of this invention is to increase the accuracy of air-to-fuel ratio control by continually correcting for the effects of offset quantities in the amplifier stage necessary to the interface circuitry. This goal is accomplished by an approach which effectively generates and subtracts these offset quantities from the processed signal.

9 Claims, 2 Drawing Sheets

METHOD AND APPARATUS FOR MAINTAINING STOICHIOMETRIC AIR-TO-FUEL RATIO IN AN INTERNAL COMBUSTION ENGINE

TECHNICAL FIELD

This invention relates generally to universal exhaust gas oxygen (UEGO) sensors and more particularly to a method and apparatus for maintaining the air-to-fuel ratio of an internal combustion engine at stoichiometric balance. A self-calibrating amplifier circuit according to the invention is disclosed which serves as an interface between an oxygen sensor and related control circuitry. The amplifier circuit is particularly well-suited to this application due to its ability to compensate for induced d.c. offsets.

BACKGROUND ART

By design, internal combustion engines exhaust gaseous emissions. Such emissions generally include nitrous oxides (NOX), hydrocarbons (HC) and carbon monoxide (CO). Although the emissions are generally not harmful, increased environmental and health concerns on the part of state and federal legislators has resulted in the promulgation of regulations which place severe limitations on the maximum allowable exhaust emissions for varying classes of vehicles operative by internal combustion engines. It is thus desirable for vehicle manufacturers to produce vehicles which have exhaust emissions within prescribed limitations.

One known method of emission control involves the use of a catalytic converter to remove emission components before they are emitted into the atmosphere. Those skilled in the art will recognize, however, that efficient operation of such catalytic converters strictly depends upon proper adjustment of the air-to-fuel mixture used by the engine. For example, catalytic converters are known to have decreased efficiency for removing NOX from engine exhaust as air-to-fuel mixtures become lean. Similarly, converter efficiency is lost for removing HC and CO when engine air-to-fuel mixtures are rich. It is thus understood by those skilled in the art that maximum converter efficiency can be achieved in all respects when the air-to-fuel mixtures is at or near stoichiometric balance.

Devices for measuring the concentration of oxygen in a mixture of gases are disclosed in U.S. Pat. Nos. 4,897,174 to Wang, et al.; 4,915,814 to Harada, et al.; 5,039,972; 5,037,526; and 5,031,445 to Kato, et al.; and 4,990,235 to Chujo. Each of these patents describe a sensor whose electrical properties (e.g., voltage, resistance, etc.) vary in proportion to the concentration of the gas to be detected. This variation of electrical property can be measured and processed in order to generate a signal which can be used to control air-to-fuel ratio.

U.S. Pat. Nos. 4,891,122 to Danno, et al., and 4,891,121 to Hirako, et al., disclose a sensor unit comprising a detecting chamber with a sensing cell, a pumping cell and a heater in combination with interface circuitry for the generation of processed output signals. As disclosed in the Danno and Hirako references, the heater maintains the sensing cell and detecting chamber at the proper temperature. Closed-loop control circuitry uses the output of the sensing cell to control the pumping cell current. This control system pumps ionized oxygen alternately in and out of the detecting chamber to maintain stoichiometric balance. The magnitude of the pumping cell current is used to measure the deviation of the measured gas from stoichiometry and is measured through the use of undisclosed voltage detecting and adding circuits connected to a series current-sensing resistor. The sign of the current is used to indicate alternately an excess or lack of oxygen and is likewise measured via a voltage comparator.

Similar to the devices described by U.S. Pat. Nos. 4,891,122 to Danno, et al., and 4,891,121 to Hirako, et al., universal gas exhaust oxygen sensors (UEGO) are devices which are used to sample the exhaust gas from an internal combustion engine. Those skilled in the art will recognize that such sensors also consist of a heater, a sensing cell and a pumping cell. In operation, the pumping cell current is controlled to regulate the sensing cell voltage to a constant value (typically 450 mV). The pumping cell current signal is then proportional to the air-to-fuel ratio of the combustion mixture. This signal is typically processed and directed to control circuitry which maintains the air-to-fuel ratio at the desired balance. The accuracy of the air-to-fuel ratio control, however, can be no better than the accuracy of the measurement of the pumping cell current.

Those skilled in the art will recognize that if the pumping cell current is measured by means of a series current sensing resistor, the value of the resistance must necessarily be small since any voltage drop across the resistance changes the voltage drop across the corresponding device being measured. Similarly, the current necessary to control the pumping cell must also be small. The voltage drop across the current sensing resistor must therefore also be a small quantity. In typical UEGO applications, a difference in the air-to-fuel ratio of 0.01 could correspond to a 150 microvolt change in voltage across the current sensing resistor. If the air-to-fuel ratio is controlled by means of a microprocessor or microcontroller interfaced through an analog-to-digital (A-to-D) converter, tremendous resolution would be required to react to such a change. For example, given a 0-to-5 volt input range, the number of discrete levels, L, required to be distinguished by the A-to-D converter would be:

$$L = \frac{\text{Voltage Range}}{\text{Voltage Increment}} + 1 \tag{1}$$

For the scenario above, this yields, $$L = \frac{5}{0.000150} + 1 = 33{,}334 \tag{2}$$

In the case of an N-bit A-to-D converter, N is related to the number of levels, $L_1$, by the well known relationship:

$$2^n = L \tag{3}$$

or, $$n = \log_2(L) = 15.025 \tag{4}$$

Rounding to the nearest integer, it is readily seen that a 16-bit A-to-D converter would thus be required to achieve this resolution.

A simpler solution exists. If the voltage signal which represents the pumping cell current is amplified prior to A-to-D conversion then less resolution is required since the Voltage Increment is proportionally increased by the gain of the amplifier. This amplification is a viable approach due to the wide variety of low cost operational amplifiers available. The only practical limitations are ensuring the peak-to-peak deviation of the amplified signal does not exceed the input range of the A-to-D converter and ensuring that the amplifier does not inject spurious signals of meaningful magnitude into the signal being processed. This amplification stage also provides an opportunity to perform shifting in the reference level which may be necessary due to the different voltage ranges of sensor signals and A-to-D convertor input signals.

One cause for concern and indeed a serious problem with respect to this amplification is the offset voltage induced on the output of an operational amplifier. Consider a Motorola MC1741C general purpose operational amplifier. The input offset voltage, $V_{io}$, the effective voltage from the inverting to noninverting inputs of the amplifier when these inputs are grounded, is typically 1 millivolt. If the operational amplifier is connected in the inverting configuration, then the output voltage, $V_o$, in response to a general input voltage, $V_i$, is given by $$V_o = -\left(\frac{R_f}{R_i}\right)V_i + \left(1 + \frac{R_f}{R_i}\right)V_{io} \qquad (5)$$

where $R_f$ represents the feedback resistor from the output to the inverting input, $R_i$ represents the input resistor which couples the input voltage to the inverting input of the operational amplifier, the ratio of $R_f$ to $R_i$ is the voltage gain of the circuit, and the operational amplifier is assumed to be ideal in all respects except input offset voltage.

Considering the previous example where a 150 microvolt resolution is desired from an oxygen sensing signal, and assuming a voltage gain of 50 is chosen to reduce the number of bits required of the A-to-D convertor, then the output of the operational amplifier to a hypothetical 150 microvolt signal is equal to $$V_o = -7.5 \text{ millivolts} \qquad (6)$$

in the ideal case where the input offset voltage is zero. If, however, the input offset voltage is equal to the typical value of 1 millivolt, the output voltage becomes $$V_o = -7.5 \text{ millivolts} + 51 \text{ millivolts} = 43.5 \text{ millivolts}, \qquad (7)$$

a significant difference. In the application of air-to-fuel ratio control, this difference would cause the controller to believe that the mixture was rich when in fact, the mixture was lean. In overall effect, the air-to-fuel controller would attempt to regulate the output voltage to zero. This would require an input voltage of 1.02 millivolts. Thus, the controller would attempt to maintain the air-to-fuel ratio at a value approximately 1% from stoichiometry. This problem is exacerbated due to the presence of other offset errors within the operational amplifier including the input offset current, and the input bias current.

Theoretically, the effects of these induced offset errors could be eliminated by individually calibrating each amplifier using simple offset null circuitry. This solution would be costly in production and practically, the effects of these errors would remain since each of the offset quantities is dependent upon temperature. As the temperature of the interface circuitry drifts, the offset voltage would likewise drift from any preset calibration point. Over an automotive temperature range of $-40°$ C. to $85°$ C. the drift of the offset voltages and currents due to temperature could be greater than the magnitude of the typical offset quantities at room temperature. The accuracy of the air-to-fuel ratio controller is limited by these effects.

SUMMARY OF THE INVENTION

The present invention overcomes the resolution difficulties of the prior art by providing a self-calibrating buffer amplifier circuit which serves as an interface between the universal exhaust gas oxygen sensor and related control circuitry. The amplifier circuit of the present invention couples and processes a voltage signal proportional to pumping cell current to a level and reference voltage suitable for input to an A-to-D converter. Because the voltage signal representing the pumping cell current is amplified prior to A-to-D conversion, less resolution is required since the voltage increment is proportionally increased by the gain of the amplifier.

In operation, the amplifier circuit of the present invention increases the accuracy of air-to-fuel ratio control by continually correcting for the effects of offset quantities. In a first calibration mode, the interface circuit input is shorted yielding a zero volt signal on the output of the interface circuit. In a second sensing mode, the input of the interface circuit is switched to measuring the pumping cell current. The difference between the sensing mode and the calibration mode measurement is then created. Since offset errors are present in both modes of operation, the effects of these offset errors are eliminated giving a true measurement of the pumping cell current. This value is held by sample and hold circuitry for A-to-D conversion by the microprocessor for eventual control of the air-to-fuel mixture.

It is thus a general object of the invention to control the air-to-fuel ratio of an internal combustion engine at stoichiometric balance.

Yet another general object of the present invention is to provide an interface between a universal exhaust gas oxygen sensor and an A-to-D converter used by a microprocessor in a closed loop control algorithm.

A more specific object of the present invention is to amplify a signal from a universal exhaust gas oxygen sensor and hold this value for reading by an A-to-D converter.

Yet another more specific object of the present invention is to correct for the offset errors in the amplifier such that the signal provided the A-to-D converter is truly proportional to the universal exhaust gas oxygen sensor signal.

BEST MODE FOR CARRYING OUT THE INVENTION

Figure 1:
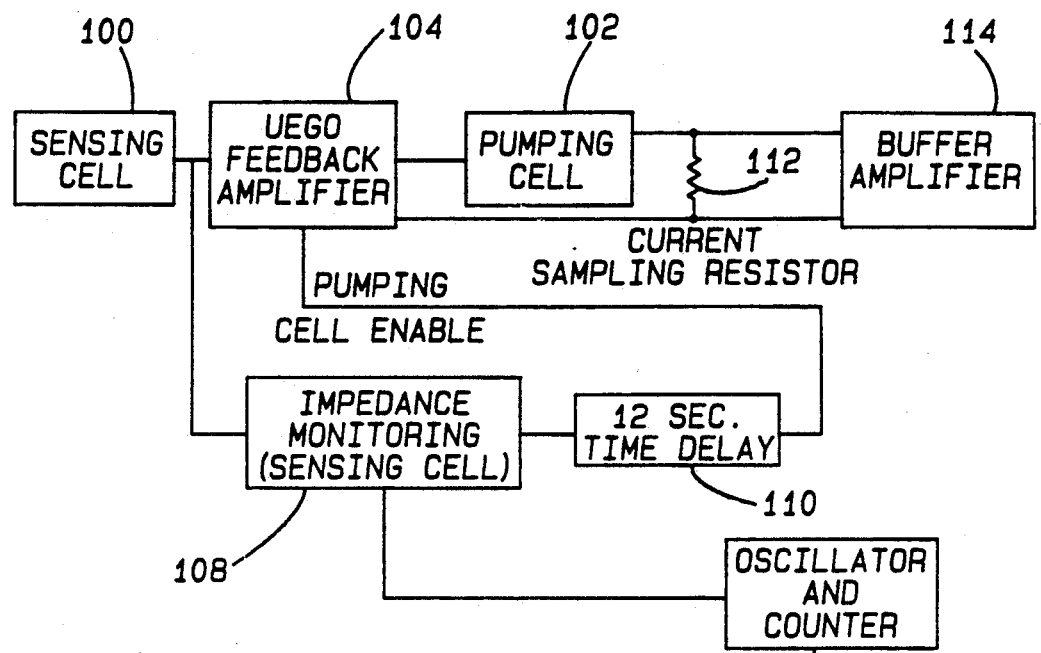
FIG. 1 is a block diagram representation of the air-to-fuel ratio control system in the present invention.

The block diagram of the full universal exhaust gas oxygen sensor interface is shown in FIG. 1. The sensing cell 100 and the pumping cell 102 are contained within the universal exhaust gas oxygen sensor as discussed previously. The UEGO feedback amplifier 104 is a PID controller that closes the loop between the sensing cell and the pumping cell. This controller observes the sensing cell voltage and delivers the appropriate magnitude and polarity of pumping cell current to cause the sensing cell voltage to be regulated to 450 mv. The pumping cell enable 106 is an additional amplifier input which prevents amplification of voltage to the pumping cell before the UEGO has warmed up. This prevention is accomplished by the impedance monitoring circuit 108 and the 12 second time delay 110. The impedance monitoring circuit uses a 500 hz square from the oscillator and counter 116, which is coupled through a high impedance to the sensing cell to monitor the output across the sensing cell 100. When the output is sufficiently low indicating a high temperature, the 12 second time delay is initiated. After the delay, power can be applied to the pumping cell and the closed loop control system can be initiated.

A 10 ohm resistor 112 is placed in series with the pumping cell to sense the pumping cell current. The present invention is represented by a buffer amplifier 114 which amplifies the voltage across the sensing resistor and shifts the reference level of said voltage to a 2.5 volt level to be read by an analog to digital converter. The resulting digital level is fed to a microprocessor which uses this value to calculate the proper air to fuel ratio control signal.

Figure 2:
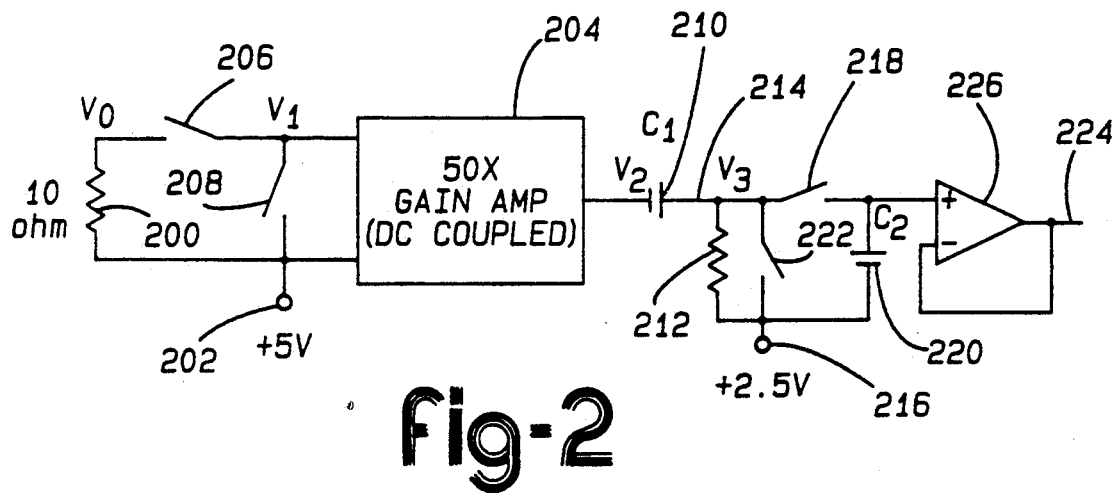
FIG. 2 is combination schematic and block diagram representation of the buffer amplifier circuit of the present invention.
Figure 3:
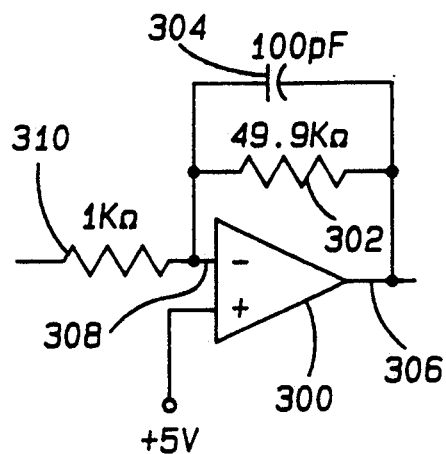
FIG. 3 is a schematic diagram of the inverting amplifier circuit of the present invention.

Referring to FIG. 2, the 10 ohm current sampling resistor 200, (the resistor 112 in FIG. 1) is placed in series with the pumping cell and connected to a five-volt power supply 202. This resistor is coupled to the input of an amplifier 204 by series analog switch means 206 and shorting analog switch means 208. The amplifier consists of an operational amplifier 300 as shown in FIG. 3 and is connected in the inverting configuration with a 49.9 kilo-ohm feedback resistor 302 and a 100 picofarad filter capacitor 304 connecting the output of the operational amplifier 306 to the inverting input 308 and a 1 kilo-ohm resistor 310 coupling the input to the inverting input. Referring back to FIG. 2, the output of the inverting amplifier 204 is coupled via coupling capacitor C1, 210 to a resistor R, 212, which is connected to 2.5 volt separate power source 216. Voltage 214 is $v_3$ across resistor R, 212. Analog switching means 218 connects said coupled output $v_3$ to an operational amplifier configured as a non-inverting buffer with its output fed directly to its inverting input and in addition with capacitor C2, 220 connected between the non-inverting input and the 2.5 volt reference 216. Analog switch means 222 shorts said coupled output $v_3$ to the 2.5 volt reference 216. The output of inverting buffer 224 is connected directly to the input of an A-to-D converter.

The circuit operates in the calibration mode when switches 206 and 218 are open and switches 208 and 222 are closed. The inverting and the noninverting inputs of the operational amplifier are shorted by switch 208. The output of the amplifier would be zero if it were ideal. However, the various sources of offset errors such as the input offset voltage and the input bias and offset currents, combine to yield an output, $v_{os}$ which is generally nonzero. In terms of FIG. 2, $$v_2 = v_{os} \tag{8}$$

The voltage $v_3$ is shorted to the 2.5 volt reference voltage by switch 222. Thus, $$v_3 = 2.5 \text{ volts.} \tag{9}$$

The voltage drop across capacitor C1, 210 is the difference between the voltages $v_3$ and $v_2$. At steady state conditions in the calibration mode this voltage becomes $$v_3 - v_2 = 2.5 \text{ volts} - v_{os}. \tag{10}$$

Measurement of the pumping cell current is effectuated by opening switches 208 and 222 and, a short time later, closing switches 206 and 218. This puts the circuit in the sensor mode. The input of the amplifier becomes the voltage drop across the pumping cell current sensing resistor, referenced to a +5 volt level. Thus, if the voltage $v_o$ were 4.99 volts referenced to a zero volt ground, $v_o$ would be −0.01 volts as referenced to a +5 volt level. The input to the amplifier $v_1$ is equal to $v_o$ as long as switch 206 is closed. In this mode, the output of the amplifier $v_2$ would be equal to $$v_2 = -49.9v_1 + v_{os}. \tag{11}$$

Notice that the output offset voltage, though capable of drifting with respect to time, is a slowly timing varying quantity. This means that the output offset voltage as expressed in Equation 10, an instant before the circuit is switched from calibration mode to sensor mode, is substantially equal to the output offset voltage as expressed in Equation 11, an instant after the sensor mode begins.

Figure 4:
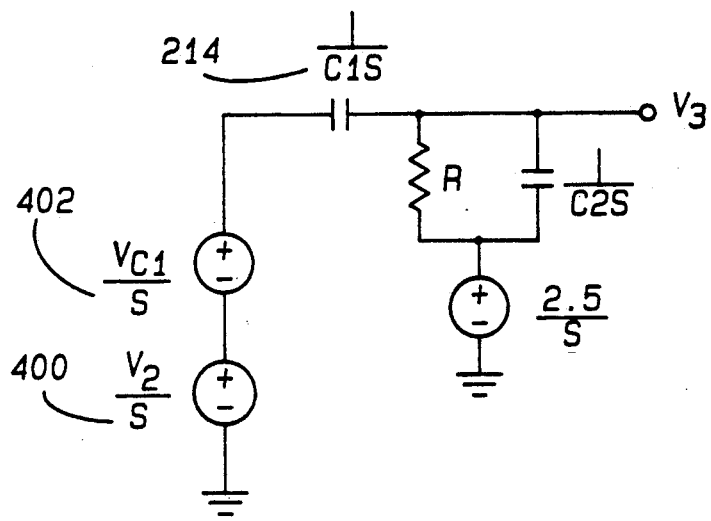
FIG. 4 is a schematic diagram of an equivalent circuit of the buffer amplifier circuit of the present invention expressed in the LaPlace Transform domain.

In sensor mode, the voltage $v_3$ is no longer shorted to the 2.5 volt reference and is allowed to float. This node is now a.c. coupled to the 2.5 volt reference by capacitor C2, 220 due to the closing of 218. The voltage $v_3$ can be calculated based upon the equivalent circuit shown in FIG. 4 where $v_2$, 400 is given in Equation 11, and each of the corresponding quantities are expressed in terms of their respective Laplace transformation. The voltage $v_{c1}$, 402 and the corresponding voltage source represent the initial voltage on the capacitor C1, 214. From Equation 10, this quantity can be expressed as $$v_{c1} = 2.5 \text{ volts} - v_{os}. \tag{12}$$

Figure 5:
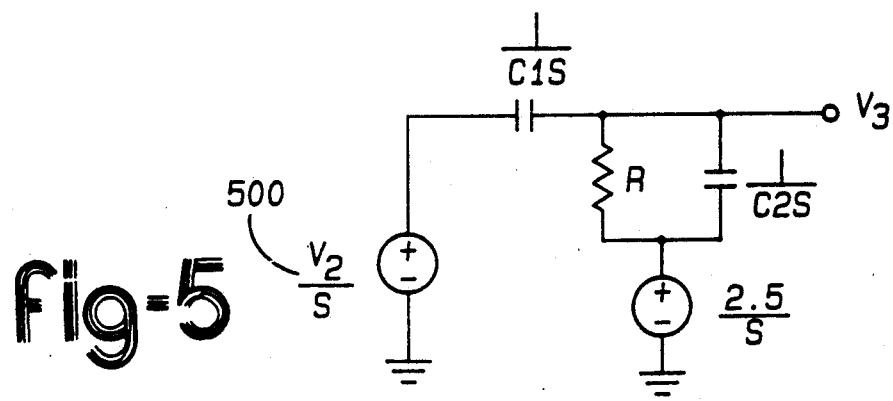
FIG. 5 is a schematic diagram of a second equivalent circuit of the buffer amplifier circuit of the present invention expressed in the Laplace Transform domain.

Notice that the initial voltage on the capacitor and the output voltage of the amplifier can be combined to form a single source 500, as shown in FIG. 5. Solving for $v_2'$ yields $$v_2' = 2.5 \text{ volts} - v_{os} - 49.9v_o + v_{os}. \tag{13}$$

The offset voltage terms cancel giving, $$v_2' = 2.5 \text{ volts} - 49.9v_o \tag{14}$$

Hence, the effects of the offset Voltage are effectively removed.

Solving for the transform voltage, $V_3(s)$, yields $$V_3(s) = \frac{V_2'\left(\frac{C1}{C1+C2}\right)}{s+\frac{1}{R(C1+C2)}} + \frac{2.5\left(\frac{C2}{C1+C2}\right)\left(s+\frac{1}{R.C2}\right)}{s+\frac{1}{R(C1+C2)}} \quad (15)$$

or, $$V_3(s) = \frac{\left(\frac{1}{C1+C2}\right)\left(C1 \cdot v_2' \cdot s + 2.5 \cdot C2\left(s+\frac{1}{RC2}\right)\right)}{s\left(s+\frac{1}{R(C1+C2)}\right)} \quad (16)$$

The value of $v_3$ at an instant in time after the switch from the calibration mode to the sensor mode (to be referred to as $v_3(0+)$ can be found using the well-known initial value theorem:

$$v_3(0^+) = \lim_{s\to\infty}(sV_3(s)) = v_2'\left(\frac{C1}{C1+C2}\right) + 2.5\left(\frac{C2}{C1+C2}\right) \quad (17)$$

If C1, 210 is chosen to be much greater than C2, 220 then the value above can be approximated by $$v_3(0^{30}) \approx v_2' \cdot 1 + 2.5 \cdot 0 = v_2' = 2.5 \text{ volts} - 49.9v_o \quad (18)$$

Thus, an instant of time after the circuit is switched to sensor mode, the voltage $v_3$ takes on an amplified value of the voltage to be measured, negated and shifted by the 2.5 volt reference voltage.

Switching back to the calibration mode, the capacitor C2, 220 and operational amplifier 226 provide a sample-and-hold function which holds the value of $v_3$. The output of the sample-and-hold circuit is then suitable for sampling by an A-to-D converter with an input range of 0-to-5 volts.

While the best mode for carrying out the invention has been described in detail, those familiar with the art to which this invention relates will recognize various alternative designs and embodiments for practicing the invention as defined by the following claims.

I claim:

1. A control arrangement for determining the air-to-fuel ratio of a fuel mixture in an internal combustion engine, including an analog-to-digital converter and a gas sensor having a sensing cell and a pumping cell, and a buffer amplifier, the control arrangement comprising:
   current detection means in electrical contact with the pumping cell for detecting pumping cell current and generating an electrical signal corresponding thereto;
   amplifier means in electrical contact with said current detection means for receiving and amplifying said electrical signal, said amplifier means having an inherent voltage offset;
   calibration means in electrical contact with said amplifier means for receiving said amplified electrical signal and substantially eliminating said voltage offset;
   reference voltage shifting means in electrical contact with said amplifier means for adjusting the DC level of said electrical signal in accordance with the operation requirements of the analog-to-digital converter;
   sample-and-hold means in electrical contact with said amplifier means and the analog-to-digital converter for selectively sampling and holding said shifted electrical signal.

2. A control arrangement as in claim 1, wherein said current detection means comprises a resistor.

3. A control arrangement as in claim 1, wherein said amplifier means comprises an operational amplifier.

4. A control arrangement as in claim 1, wherein said reference voltage shifting means comprises a voltage source used as an input to an operational amplifier.

5. A control arrangement as in claim 1 wherein said sample-and-hold means comprises:
   a capacitor;
   a high input-impedance operational amplifier in electrical contact with said capacitor; and
   switch means in electrical contact with said capacitor and said operation amplifier for disconnecting said capacitor from said operational amplifier.

6. A method for controlling the air-to-fuel ratio of an internal combustion engine, the method comprising the steps of:
   providing an analog-to-digital converter;
   providing a gas sensor having a sensing cell and a pumping cell;
   detecting current through said pumping cell;
   generating an electrical signal corresponding to said detected pumping cell current;
   providing amplifier means having an inherent voltage offset, said amplifier means in electrical contact with said pumping cell;
   amplifying said electrical signal;
   processing said amplified electrical signal to substantially eliminate said voltage offset and adjust the D.C. level of said signal in accordance with the operational requirements of said analog-to-digital converter.

7. The method as in claim 6, wherein the method further includes the step of sampling said processed amplified electrical signal and holding the signal for input to said analog-to-digital converter.

8. A control arrangement for determining the air-to-fuel ratio of a fuel mixture in an internal combustion engine, including an analog-to-digital converter and a gas sensor having a sensing cell and a pumping cell, and a buffer amplifier, the control arrangement comprising:
   current detection means in electrical contact with the pumping cell for detecting pumping cell current and generating an electrical signal corresponding thereto;
   an operational amplifier in electrical contact with said current detection means for receiving and amplifying said electrical signal, said operational amplifier having an inherent voltage offset;
   calibration means in electrical contact with said operational amplifier for receiving said amplified electrical signal and substantially eliminating said voltage offset;
   a voltage source in electrical contact with said operational amplifier for adjusting the DC level of said electrical signal in accordance with the operation requirements of the analog-to-digital converter;
   sample-and-hold means in electrical contact with said operational amplifier and the analog-to-digital converter for selectively sampling and holding said shifted electrical signal.

9. A control arrangement as in claim 8 wherein said sample-and-hold means comprises:
a capacitor;
a high input-impedance operational amplifier in electrical contact with said capacitor; and
switch means in electrical contact with said capacitor and said operational amplifier for disconnecting said capacitor from said operational amplifier.

* * * * *

UNITED STATES PATENT AND TRADEMARK OFFICE
CERTIFICATE OF CORRECTION

PATENT NO. : 5,211,154
DATED : May 18, 1993
INVENTOR(S) : Arnold W. Brandt It is certified that error appears in the above-identified patent and that said Letters Patent is hereby corrected as shown below:

Column 2, line 8, after "and" delete "4,891,121" and substitute --4,891,121--.

Column 7, Equation No. 18, delete:

"$v_3(O^{30}) \approx v_2' * 1 + 2.5 * 0 = v_2' \; 2.5 \; volts - 49.9 v_o$"

and substitute:

-- $v_3(O^+) \approx v_2' * 1 + 2.5 * 0 - v_2' \; -2.5$ --.

Signed and Sealed this

Tenth Day of May, 1994

BRUCE LEHMAN

*Attest:*

*Attesting Officer*   *Commissioner of Patents and Trademarks*